US009623023B2

(12) United States Patent
Bhide et al.

(10) Patent No.: US 9,623,023 B2
(45) Date of Patent: Apr. 18, 2017

(54) CLASS OF NON-STIMULANT TREATMENT AND ADHD AND RELATED DISORDERS

(71) Applicants: The Florida State University Research Foundation, Incorporated, Tallahassee, FL (US); The General Hospital Corporation, Boston, MA (US)

(72) Inventors: Pradeep G. Bhide, Tallahassee, FL (US); Jinmin Zhu, Tallahassee, FL (US); Joseph Biederman, Brookline, MA (US); Thomas J. Spencer, Carlisle, MA (US)

(73) Assignees: The Florida State University Research Foundation, Incorporated, Tallassee, FL (US); The General Hospital Corporation, Boston, MA (US)

( * ) Notice: Subject to any disclaimer, the term of this patent is extended or adjusted under 35 U.S.C. 154(b) by 260 days.

(21) Appl. No.: 14/027,676

(22) Filed: Sep. 16, 2013

(65) Prior Publication Data
US 2014/0113924 A1 Apr. 24, 2014

Related U.S. Application Data

(60) Provisional application No. 61/716,769, filed on Oct. 22, 2012.

(51) Int. Cl.
A61K 31/485 (2006.01)
(52) U.S. Cl.
CPC .................. A61K 31/485 (2013.01)
(58) Field of Classification Search
CPC ................................... A61K 31/485
See application file for complete search history.

(56) References Cited

U.S. PATENT DOCUMENTS

2007/0213644 A1* 9/2007 Pagel .................. A61H 1/0266
601/23

FOREIGN PATENT DOCUMENTS

WO WO 2011020030 A2 * 2/2011 ........... A61K 31/135

OTHER PUBLICATIONS

Recant, L., Voyles, N. R., et al. "Naltrexone reduces weight gain, alters "beta-encorphin", and reduces insulin output from pancreatic islets of genetically obese mice," Peptides 1(4): 309-13 (1980).
Ren, J. Q., Jiang, Y., et al. "Prenatal L-DOPA exposure produces lasting changes in brain dopamine content, cocaine-induced dopamine release and cocaine conditioned place preference." Neuropharmacology 60(2-3): 295-302 (2011).
Robbins, T. W. "ADHD and addiction." Nat. Med. 8(1): 24-25 (2002).
Russell, V. A., Sagvolden, T., et al. "Animal models of attention-deficit hyperactivity disorder." Behav. Brain Funct. 1: 9 (2005).
Sagvolden, T., Russell, V. A., et al. "Rodent models of attention-deficit/hyperactivity disorder." Biol. Psychiatry 57(11): 1239-47 (2005).
Sagvolden T, Johansen EB, Woien G, Walaas SI, Storm-Mathisen J, Bergersen LH, Hvalby O, Jensen V, Aase H, Russell VA, Killeen PR, Dasbanerjee T, Middleton FA, Faraone SV, "The spontaneously hypertensive rat model of ADHD—the importance of selecting the appropriate reference strain," Neuropharmacology 57:619-626 (2009).
Schneider, T., Ilott, N., et al. "Prenatal exposure to nicotine impairs performance of the 5-choice serial reaction time task in adult rats." Neuropsychopharmacology 36(5): 1114-25 (2011).
Soderman, A. R. and Unterwald, E. M. "Cocaine reward and hyperactivity in the rat: sites of mu opioid receptor modulation." Neuroscience 154(4): 1506-16 (2008).
Svingos, A. L., Chavkin, C., et al. "Major coexpression of kappa-opioid receptors and the dopamine transporter in nucleus accumbens axonal profiles." Synapse 42(3): 185-92 (2001).
Svingos, A. L., Garzon, M., et al. "Mu-opioid receptors in the ventral tegmental area are targeted to presynaptically and directly modulate mesocortical projection neurons." Synapse 41(3): 221-29 (2001).
Svingos, A. L. and Colago, E. E. "Kappa-Opioid and NMDA glutamate receptors are differentially targeted within rat medial prefrontal cortex." Brain Res. 946(2): 262-71 (2002).
Takemori, A. E., Ho, B. Y., et al. "Nor-binaltorphimine, a highly selective kappa-opioid antagonist in analgesic and receptor binding assays." J. Pharmacol. Exp. Ther. 246(1): 255-58 (1988).
Thompson, A. C., Zapata, A., et al. "Kappa-opioid receptor activation modifies uptake in the nucleus accumbens and opposes the effects of cocains." J. Neurosci. 20(24): 9333-40 (2000).
Todtenkopf, M. S., Marcus, J. F., et al. "Effects of kappa-opioid receptor ligands on intracranial self-stimulation in rats." Psychopharmacology (Berl) 172(4): 463-70 (2004).
Varaschin, R. K. and Morato, G. S. "Selective mu- and kappa-opioid receptor antagonists administered into the nucleus accumbens interfere with rapid tolerance to ethanol in rats." Psychopharmacology (Berl) 206(1): 85-96 (2009).
Volkow N.D., Fowler J. S., Gatley SJ, Dewey SL, Wang GJ, Logan J, Ding YS, Franceschi D, Gifford A, Morgan A, Pappas N, King P, "Comparable changes in synaptic dopamine induced by methylphenidate and by cocaine in the baboon brain." Synapse 31:59-66 (1999).
Volkow, N. D., Wang, G. J., et al. "Methylphenidate and cocaine have a similar in vivo potency to block dopamine transporters in the human brain." Life Sci. 65(1): PL7-12 (1999).
Volkow, N. D. "Stimulant medications: how to minimize their reinforcing effects?" Am. J. Psychiatry 163(3): 359-61 (2006).
Wickstrom, R. "Effects of nicotine during pregnancy: human and experimental evidence." Current neuropharmacology 5(3): 213-22 (2007).
Wiley, M. D., Poveromo, L. B., et al. "Kappa-opioid system regulates the long-lasting behavioral adaptations induced by early-life exposure to methylphenidate." Neuropsychopharmacology 34(5): 1339-50 (2009).

(Continued)

*Primary Examiner* — Sreeni Padmanabhan
*Assistant Examiner* — Jody Karol
(74) *Attorney, Agent, or Firm* — Clark & Elbing LLP

(57) ABSTRACT

Described is a method of administering nor-binaltorphimine (nor-BNI) or a nor-BNI analog to an individual having Attention Deficit/Hyperactivity Disorder (ADHD) to thereby reduce the effects of ADHD in the individual.

18 Claims, 4 Drawing Sheets

(56) References Cited

OTHER PUBLICATIONS

Willemsen-Swinkels, S. H., Buitelaar, J. K., et al. "The effects of chronic naltrexone treatment in young autistic children: a double-blind placebo-controlled crossover study." Biol. Psychiatry 39(12): 1023-31 (1996).
Yano, M. and Steiner, H. "Methylphenidate and cocaine: the same effects on gene regulation?" Trends Pharmacol. Sci .28(11): 588-596 (2007).
You, Z. B., Herrera-Marschitz, M., et al. "Modulation of neurotransmitter release in the basal ganglia of the rat brain by dynorphin peptides." J. Pharmacol. Exp. Ther. 290(3): 1307-15 (1999).
Zagon, I. S. "Endogenous opioids, opioid receptors, and neuronal development." NIDA Res. Monogr. 78: 61-71 (1987).
Zagon, I. S. and McLaughlin, P. J. "Increased brain size and cellular content in infant rats treated with an opiate antagonist." Science 221(4616): 1179-80 (1983).
Zagon, I. S. and McLaughlin, P. J. "Naltrexone modulates growth in infant rats." Life Sci. 33(24): 2449-54 (1983).
Zagon, I. S. and McLaughlin, P. J. "Endogenous opioid systems regulate cell proliferation in the developing rat brain." Brain Res. 412(1): 68-72 (1987).
Zhang, L., Shirayama, Y., et al. "Minocycline attenuates hyperlocomotion and prepulse inhibition deficits in mice after administration of the NMDA receptor antagonist dizocilpine." Neuropsychopharmacology 32(9): 2004-10 (2007).
Zhu, J. M., X. P. He, et al. "Changes of releases of beta-endorphin-like immunoreactive substances and noradrenaline in rabbit's preoptic area during acupuncture analgesia." Sheng Li Xue Bao 42(2): 188-93 (1990).
Zhu, J., Chen, C. et al. "Cloning of a human kappa opioid receptor from the brain." Life Sci. 56(9): PL201-07 (1995).
Zhu, J., Xue, J. C., et al. "The region in the mu opioid receptor conferring selectivity for sufentanil over the delta receptor is different from that over the kappa receptor." FEBS Lett. 384(2): 198-202 (1996).
Zhu, J., Spencer, T. J., et al. "Methylphenidate and mu opioid receptor interactions: a pharmacological target for prevention of stimulant abuse." Neuropharmacology 61(1-2): 283-92 (2011).
Zhu, J., Zhang, X., et al. "Prenatal nicotine exposure mouse model showing hyperactivity, reduced cingulate cortex volume, reduced dopamine turnover, and responsiveness to oral methylphenidate treatment." J. Neurosci. 32(27): 9410-18 (2012).
Zuvekas, S. H., Vitiello, B., et al. "Recent trends in stimulant medication use among U.S. children." Am. J. Psychiatry 163(4): 579-85 (2006).
Balcioglu, A., Ren, J-Q., McCarthy, D.M., Spencer, T. J., Biederman, J., Bhide, P. G. Plasma and brain concentrations of oral therapeutic doses of methylphenidate and their impact on brain monoamind content in mice. Neuropharmacology 102:783-88 (2009).
Bergman, J., Madras, B. K., et al. "Effects of cocaine and related drugs in nonhuman primates. III. Self-administration by squirrel monkeys." J. Pharmacol. Exp. Ther. 251(1): 150-55 (1989).
Bhargava, H. N., Gulati A, "Kappa opioid receptor activity in spontaneously hypertensive rats," The Journal of Pharmacology and Experimental Therapeutics 245:460-465 (1988).
Biederman, J., T. Wilens, et al. "Is ADHD a risk factor for psychoactive substance use disorders? Findings from a four-year prospective follow-up study." J. Am. Acad. Child. Adolesc. Psychiatry 36(1): 21-29 (1997).
Biederman, J., Wilens, T. E., et al. "Does attention-deficit hyperactivity disorder impact the developmental course of drug and alcohol abuse and dependence?" Biol. Psychiatry 44(4): 269-73 (1998).
Biederman, J. "Attention-deficit/hyperactivity disorder: a selective overview." Biol Psychiatry 57(11): 1215-20 (2005).
Bolanos, C. A., Garmsen, G. M., et al., "Effects of the kappa-opioid receptor agonist U-50,488 on morphine-induced place preference conditioning in the developing rat." Eur. J. Pharmacol. 317(1): 1-8 (1996).
Bright, G. M. "Abuse of medications employed for the treatment of ADHD: results from a large-scale community survey." Medscape J. Med. 10(5): 111(2008).
Broom, D. C., Jutkiewicz, E. M., et al. "Nonpeptidic delta-opioid receptor agonists reduce immobility in the forced swim assay in rats." Neuropsychopharmacology 26(6): 744-55, (2002).
Brown, R. T., Amler, R. W., et al. "Treatment of attention-deficit/hyperactivity disorder: overview of the evidence." Pediatrics 115(6): e749-57 (2005).
Bryant, C. D., Roberts, K. W., et al. "Pavlovian conditioning of multiple opioid-like responses in mice." Drug Alcohol Depend. 103(1-2): 74-83 (2009).
Campbell, M., Anderson, L. T., et al. "Naltrexone in autistic children: behavioral symptoms and attentional learning." J. Am. Acad. Child Adolesc. Psychiatry 32(6): 1283-91 (1993).
Carlezon, W. A., Jr., Beguin, C., et al. "Depressive-like effects of the kappa-opioid receptor agonist salvinorin A on behavior and neurochemistry in rats." J. Pharmacol. Exp. Ther. 316(1): 440-47 (2006).
Chefer, V. I., Moron, J. A., et al. "Kappa-opioid receptor activation prevents alterations in mesocortical dopamine neurotransmission that occur during abstinence from cocaine." Neuroscience 101(3): 619-27 (2000).
Cummings, J. L. "Frontal-subcortical circuits and human behavior." Arch. Neurol. 50(8): 873-80 (1993).
Dean, R. L., Todtenkopf, M. S. et al. "Overriding the blockade of antinociceptive actions of opioids in rats treated with extended-release naltrexone." Pharmacol. Biochem. Behav. 89(4): 515-22 (2008).
Di Chiara, G. and Imperato, A. "Drugs abused by humans preferentially increase synaptic dopamine concentrations in the mesolimbic system of freely moving rats." Proc. Natl. Acad. Sci. USA 85(14): 5274-78 (1988).
Donahue, R. N., McLaughlin, P. J., et al. "Low-dose naltrexone targets the opioid growth factor-opioid growth factor receptor pathway to inhibit cell proliferation: mechanistic evidence from a tissue culture model." Exp. Biol. Med. (Maywood) 236(9): 1036-50 (2011).
Drake, C. T., Patterson, T. A., et al. "Kappa opioid receptor-like immunoreactivity in guinea pig brain: ultrastructural localization in presynaptic terminals in hippocampal formation." J. Comp. Neurol. 370(3): 377-95 (1996).
Elchaar, G. M., Maisch, N. M., et al. "Efficacy and safety of naltrexone use in pediatric patients with autistic disorder." Ann. Pharmacother. 40(6): 1086-95 (2006).
Endoh, T., Matsuura, H., et al. "Nor-binaltorphimine: a potent and selective kappa-opioid receptor antagonist with long-lasting activity in vivo." Arch. Int. Pharmacodyn. Ther. 316: 30-42 (1992).
Evans, C. J.,. Keith, D. E.,Jr., et al. "Cloning of a delta opioid receptor by functional expression." Science 258(5090): 1952-55 (1992).
Feldman, H. M., Kolmen, B. K., et al. "Naltrexone and communication skills in young children with autism." J. Am. Acad. Child Adolesc. Psychiatry 38(5): 587-93 (1999).
Gerasimov, A. A. and Volkova, A. M. "[Treatment of patients with lumbar osteochondrosis by the method of intra-tissular electric stimulation]." Ortop. Travmatol. Protez. (5): 13-17 (1991).
Hauser, K. F., McLaughlin, P. J., et al. "Endogenous opioids regulate dendritic growth and spine formation in developing rat brain." Brain Res. 416(1): 157-61 (1987).
Hellman, K. M., Mendelson, S. J., et al. "Opioid microinjection into raphe magnus modulates cardiorespiratory function in mice and rats." Am. J. Physiol. Regul. Integr. Comp. Physiol. 297(5): R1400-08 (2009).
Huizink, A. C. and Mulder, E. J. "Maternal smoking, drinking or cannabis use during pregnancy and neurobehavioral and cognitive functioning in human offspring." Neurosci. Biobehav. Rev. 30(1): 24-41 (2006).
Jomary, C., Gairin, J. E., "Synaptic localization of kappa opioid receptors in guinea pig neostriatum." Proc. Natl. Acad. Sci. USA 89(2): 564-68 (1992).

(56) References Cited

OTHER PUBLICATIONS

Jones, D. N. and Holtzman, S. G. "Long term kappa-opioid receptor blockade following nor-binaltorphimine." Eur. J. Pharmacol. 215(2-3): 345-48 (1992).
Kieffer, Befort, B. L., K., et al. "The delta-opioid receptor: isolation of a cDNA by expression cloning and pharmacological characterization." Proc. Natl. Acad. Sci. USA 89(24): 12048-52 (1992).
Klein-Schwartz, W. "Abuse and toxicity of methylphenidate." Curr. Opin. Pediatr. 14(2): 219-23 (2002).
Knoll, A. T., Meloni, E. G., et al. "Anxiolytic-like effects of kappa-opioid receptor antagonists in models of unlearned and learned fear in rats." J. Pharmacol. Exp. Ther. 323(3): 838-45 (2007).
Kuczenski, R. and Segal, D. S. "Locomotor effects of acute and repeated threshold doses of amphetamine and methylphenidate: relative roles of dopamine and norepinephrine." J. Pharmacol. Exp. Ther. 296(3): 876-83 (2001).
Kuczenski, R. and Segal, D. S. "Exposure of adolescent rats to oral methylphenidate: preferential effects on extracellular norepinephrine and absence of sensitization and cross-sensitization to methamphetamine." J. Neurosci. 22(16): 7264-71 (2002).
Kuczenski, R. and Segal, D. S. "Stimulant actions in rodents: implications for attention-deficit/hyperactivity disorder treatment and potential substance abuse." Biol. Psychiatry 57(11): 1391-96 (2005).
Li, S., Zhu, J., et al. "Molecular cloning and expression of a rat kappa opioid receptor." Biochem. J. 295 ( Pt 3): 629-33 (1993).
Linnet, K. M., Dalsgaard, S., et al. "Maternal lifestyle factors in pregnancy risk of attention deficit hyperactivity disorder and associated behaviors: review of the current evidence." Am. J. Psychiatry 160(6): 1028-40 (2003).
Mahler, S. V. and K. C. Berridge, "What and when to "want"? Amygdala-based focusing of incentive salience upon sugar and sex." Psychopharmacology (Berl) 221(3): 407-426 (2012).
Maisonneuve, I. M., Archer, S., et al. "U50,488, a kappa opioid receptor agonist, attenuates cocaine-induced increases in extracellular dopamine in the nucleus accumbens of rats." Neurosci. Lett. 181(1-2): 57-60 (1994).

Margolis, E. B., Lock, H., et al. "Kappa opioids selectively control dopaminergic neurons projecting to the prefrontal cortex." Proc. Natl. Acad. Sci. USA 103(8): 2938-42 (2006).
McLaughlin, P. J., Sassani, J. W., et al. "Diabetic keratopathy and treatment by modulation of the opioid growth factor (OGF)-OGF receptor (OGFr) axis with naltrexone: a review." Brain Res. Bull. 81(2-3): 236-47 (2010).
Meshul, C. K. and McGinty, J. F. "Kappa opioid receptor immunoreactivity in the nucleus accumbens and caudate-putamen is primarily associated with synaptic vesicles in axons." Neuroscience 96(1): 91-99 (2000).
Metcalf MD, Coop A, "Kappa opioid antagonists: past successes and future prospects," The AAPS journal 7:E704-722 (2005).
Milberger, S., Biederman, J., et al. "Is maternal smoking during pregnancy a risk factor for attention deficit hyperactivity disorder in children?" Am. J. Psychiatry 153(9): 1138-42 (1996).
Mill, J. "Rodent models: Utility for candidate gene studies in human attention-deficit hyperactivity disorder (ADHD)." J. Neurosci. Methods 166(2):294-305 (2007).
Olfson, M., Marcus, S. C., et al. "National trends in the use of psychotropic medications by children." J. Am. Acad. Child. Adoles.c Psychiatry 41(5): 514-21 (2002).
Patrick, K. S. and Markowitz, J. S. "Pharmacology of methylphenidate, amphetamine enantiomers and pemoline in attention-deficit hyperactivity disorder." Human Psychopharmacol. 12(6): 527-46 (1997).
Patkar, K. A., Wu, J., Ganno, M. L., Singh, H. D., Ross, N. C., Rasakham, K., Toll, L., McLaughlin, J. P., "Physical Presence of Nor-Binaltorphimine in Mouse Brain over 21 Days after a Single Administration Corresponds to Its Long-Lasting Antagonistic Effect on kappa-Opioid Receptors," The Journal of pharmacology and experimental therapeutics 346:545-554 (2013).
Pauly, J. R. and Slotkin, T. A. "Maternal tobacco smoking, nicotine replacement and neurobehavioural development." Acta Paediatr. 97(10): 1331-37 (2008).
Randall-Thompson, J. F., Pescatore, K. A., et al. "A role for delta opioid receptors in the central nucleus of the amygdala in anxiety-like behaviors." Psychopharmacology (Berl) 212(4): 585-95 (2010).

\* cited by examiner

CLASS OF NON-STIMULANT TREATMENT AND ADHD AND RELATED DISORDERS

CROSS-REFERENCE TO RELATED APPLICATIONS

This application claims benefit of priority to U.S. Provisional Patent Application No. 61/716,769, entitled "NOVEL CLASS OF NON-STIMULANT TREATMENT OF ADHD AND RELATED DISORDERS" filed Oct. 22, 2012 which is incorporated herein by reference in its entirety.

STATEMENT OF JOINT RESEARCH AGREEMENT

In compliance with 37 C.F.R. §1.71(g) (1), disclosure is herein made that the inventions described and claimed herein were made pursuant to a Joint Research Agreement as defined in 35 U.S.C. 103 (c) (3), that was in effect on or before the date the inventions were made, and as a result of activities undertaken within the scope of the Joint Research Agreement, by or on the behalf of Florida State University and Massachusetts General Hospital (d.b.a. The General Hospital Corporation).

BACKGROUND

1. Field of the Invention

The present invention relates to treatments for Attention Deficit Hyperactivity Disorder (ADHD).

2. Related Art

Stimulant compounds such as methylphenidate (MPH) and amphetamine are the mainstays of treatment for Attention Deficit/Hyperactivity Disorder (ADHD). The principal mechanism of action of stimulants is blockade of the dopamine transporter and/or facilitation of dopamine release, both of which lead to increased extracellular dopamine and amelioration of the hypo-dopaminergic state associated with ADHD (Volkow Wang et al., 1999 (Reference 67); Kuczenski and Segal, 2001 (Reference 33); Kuczenski and Segal, 2005 (Reference 35); and Yano and Steiner 2007 (Reference 72). Stimulant medications share a common mechanism of action with well known addictive drugs such as cocaine namely, blockade of the dopamine transporter and facilitation of dopamine release. Therefore, stimulant medications can be addictive, and lingering concerns remain among the general public, patients, and physicians alike that stimulant medications may produce drug addiction even when taken therapeutically. The recent increase in recreational use of prescription stimulants adds to this concern (Bright, 2008 (Reference 8)); New York Times, Jun. 19, 2012). In fact, the US Drug Enforcement Agency has placed MPH and amphetamine in the same controlled substances category (Schedule II) as cocaine. An unintended consequence of these developments is that millions of children and adults that could benefit from therapeutic use of stimulants may not have access to these medications or may choose not to receive them because of concerns about their potential for addiction. Therefore, untreated ADHD remains a serious medical, educational and societal burden. Therefore, there is an urgent need to develop safe and effective, abuse-free, compounds for ADHD treatment.

SUMMARY

According to one broad aspect, the present invention provides method comprising the following step: (a) administering an effective amount of nor-binaltorphimine (nor-BNI) or a nor-BNI analog to an individual having ADHD to thereby reduce the symptoms of ADHD in the individual.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

DETAILED DESCRIPTION OF THE PREFERRED EMBODIMENTS

Definitions

Figure 1:
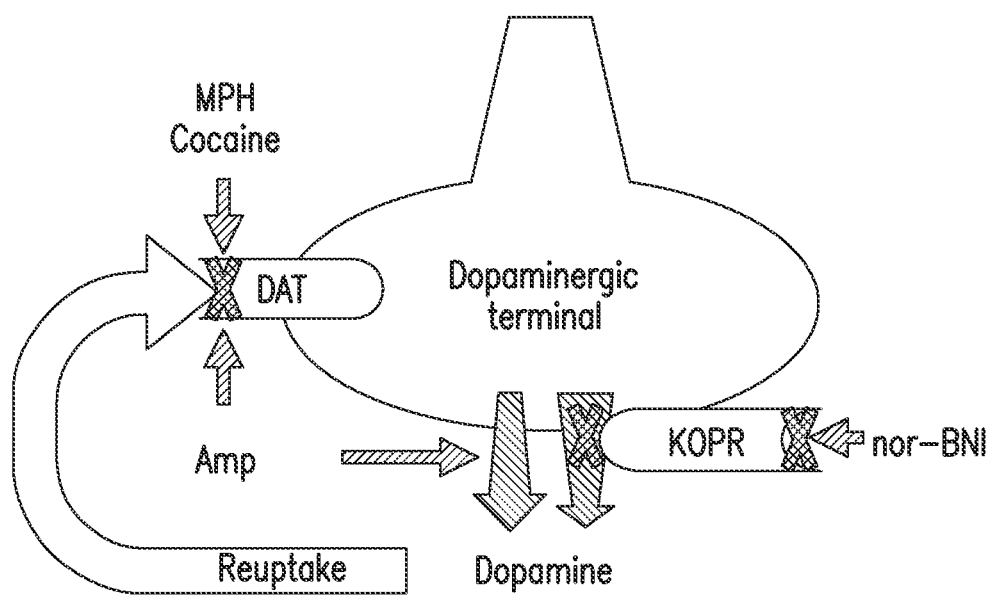
FIG. 1 is a diagram showing a mechanism of action of the KOPR antagonist nor-binaltorphimine (nor-BNI) versus that of stimulants at dopaminergic terminals.

Where the definition of terms departs from the commonly used meaning of the term, applicant intends to utilize the definitions provided below, unless specifically indicated.

For the purposes of the present invention, a value or property is "based" on a particular value, property, the satisfaction of a condition, or other factor, if that value is derived by performing a mathematical calculation or logical decision using that value, property or other factor.

For purpose of the present invention, the term "nor-BNI analog" refers to a compound with physical, chemical, biochemical, structural, functional or pharmacological properties similar to nor-BNI. Examples of nor-BNI analogs include but are not limited to: (3R)-7-Hydroxy-N-[(1S)-1-[[(3R,4R)-4-(3-hydroxyphenyl)-3,4-dimethyl-1-piperidinyl]methyl]-2-methylpropyl]-1,2,3,4-tetrahydro-3-isoquinolinecarboxamide (JDTic), Alvimopan, LY255.582, AZ-MTAB, PF4455242 and LY2456302.

For purposes of the present invention, the term "Attention Deficit/Hyperactivity Disorder (ADHD)" refers to terms such as ADHD, ADHD NOS, Hyperkinetic Disorder, Attention Deficit Disorder with and without Hyperactivity, and others, as defined by DSM III, DSM III-R, DSM IV, DSM IV-TR, DSM IV, future DSM definitions, ICD 8, ICD 9, ICD 10 and future versions of ICD as well as similar definitions of ADHD. For purposes of the present invention, the term "ADHD" includes subthreshold conditions where there are not sufficient ADHD symptoms to meet full criteria, late onset of ADHD symptoms and ADHD symptoms that occur in the context of comorbid disorders, after head trauma or due to unknown etiology.

For purposes of the present invention, the term "daily dose" refers to the total dosage amount administered to an individual in a single 24-hour day.

For purposes of the present invention, the term "dose" refers to a single administration of a drug.

For purposes of the present invention, the term "effective amount" refers to an amount nor-BNI sufficient to reduce the total score of an ADHD rating scale by an average of at least 25%.

For purposes of the present invention, the term "hypodopaminergic state" refers to a state in which there is a non-physiologically low level of dopamine present at the synapse between the axon of a neuron that produces dopamine and the dendrite or cell body of a neuron with receptors for dopamine.

For purposes of the present invention, the term "individual" refers to a mammal. For example, the term "individual" may refer to a human individual.

For purposes of the present invention, the term "intranasal delivery" and term "intranasal administration" are equivalent terms and refer to the delivery or administration of a chemical composition through one or both nasal passages of an individual. Examples of intranasal delivery include actively spraying a chemical composition containing a drug, such as nor-BNI, into a nasal passage, having an individual inhale a chemical mist containing a drug.

For purposes of the present invention, the term "mg/kg" refers to the dose of a substance administered to an individual in milligrams per kilogram of body weight of the individual.

For purposes of the present invention, the term "nasal spray" refers to a method of delivery that functions by instilling a fine mist into the nostril by action of a hand-operated pump.

For purposes of the present invention, the term "reduce the symptoms of ADHD" refers to reduction of the total score of an ADHD rating scale. ADHD rating scales are Likert scales where each symptom of ADHD is given a number based on severity, frequency or both. The ratings for each symptom are totaled to determine a total ADHD rating scale score. Examples of ADHD rating scales include but are not limited to the following scales: various versions of the Conners Rating Scales, the SNAP scale, the SKAMP scale, the SWAN scale, the ADHD RS-IV scale, the VADTRS scale, the VADPRS scale, the ADHD-SHS scale, the ADDES scale, the ACTers scale, the BADDS scale, the AISRS scale and the ADHD RS adult as well as many other similar scales. The raters for each of these scales may be a clinician or investigator, a parent, a teacher, a significant other or others.

For purposes of the present invention, the term "symptoms of ADHD" refer to symptoms defined by the various DSM and ICD versions as well as other similar definitions of ADHD described above in the definition of "ADHD." For example in DSM V the symptoms are: (1) often fails to give close attention to details or makes careless mistakes in schoolwork, at work, or during other activities (e.g., overlooks or misses details, work is inaccurate), (2) often has difficulty sustaining attention in tasks or play activities (e.g., has difficulty remaining focused during lectures, conversations, or lengthy reading), (3) often does not seem to listen when spoken to directly (e.g., mind seems elsewhere, even in the absence of any obvious distraction), (4) often does not follow through on instructions and fails to finish schoolwork, chores, or duties in the workplace (e.g., starts tasks but quickly loses focus and is easily sidetracked), (5) often has difficulty organizing tasks and activities (e.g., difficulty managing sequential tasks; difficulty keeping materials and belongings in order; messy, disorganized work; has poor time management; fails to meet deadlines), (6) often avoids, dislikes, or is reluctant to engage in tasks that require sustained mental effort (e.g., schoolwork or homework; for older adolescents and adults, preparing reports, completing forms, reviewing lengthy papers), (7) often loses things necessary for tasks or activities (e.g., school materials, pencils, books, tools, wallets, keys, paperwork, eyeglasses, mobile telephones), (8) Is often easily distracted by extraneous stimuli (for older adolescents and adults, may include unrelated thoughts), (9) is often forgetful in daily activities (e.g., doing chores, running errands; for older adolescents and adults, returning calls, paying bills, keeping appointments), (10) often fidgets with or taps hands or feet or squirms in seat, (11) often leaves seat in situations when remaining seated is expected (e.g., leaves his or her place in the classroom, in the office or other workplace, or in other situations that require remaining in place), (12) often runs about or climbs in situations where it is inappropriate. (Note: In adolescents or adults, may be limited to feeling restless), (13) often unable to play or engage in leisure activities quietly, (14) is "on the go," acting as if "driven by a motor" (e.g., is unable to be or uncomfortable being still for extended time, as in restaurants, meetings; may be experienced by others as being restless or difficult to keep up with), (15) Often talks excessively, (16), often blurts out an answer before a question has been completed (e.g., completes people's sentences; cannot wait for turn in conversation), (17) often has difficulty waiting his or her turn (e.g., while waiting in line), and (18) often interrupts or intrudes on others (e.g., butts into conversations, games, or activities; may start using other people's things without asking or receiving permission; for adolescents and adults, may intrude into or take over what others are doing.

For purposes of the present invention, the term "sprayable" refers to a solution that is turned into a fine mist by action of a hand operated pump.

Description

In one embodiment, the present invention provides kappa opioid receptor (KOPR) antagonists as a novel class of non-stimulant medication for ADHD.

In one embodiment, the present invention provides kappa opioid receptor (KOPR) antagonists as a novel class of non-dysphoric medication for ADHD.

In one embodiment, the present invention provides a combination of kappa opioid receptor (KOPR) antagonists and stimulant compounds such as MPH or amphetamine and their analogs as a novel class of medication for ADHD.

In one embodiment, the present invention provides kappa opioid receptor (KOPR) antagonists or a combination of stimulants such as MPH and amphetamine plus KOPR antagonists as a novel class of non-dysphoric medication for ADHD.

In one embodiment, the present invention provides kappa opioid receptor (KOPR) antagonists or a combination of stimulants such as MPH and amphetamine plus KOPR antagonists as a novel class of non-dysphoric medication for a subtype of ADHD that does not respond to treatment with stimulants alone.

In one embodiment, the present invention provides a single administration of kappa opioid receptor (KOPR) antagonists as an efficacious treatment for up to one month.

KOPR, $\mu$ and $\delta$ opioid receptors (MOPR and DOPR, respectively), are widely distributed in the CNS. KOPR and its endogenous ligand dynorphin are implicated in reward, motivation, mood and endocrine function (Butelman et al 2012). The KOPR-dynorphin system interacts with the dopaminergic system and facilitates, cognitive functions. KOPR is localized to pre-synaptic compartment of the meso-cortical dopaminergic axons in the prefrontal cortex (PFC), a brain region critical for cognitive functions, especially attention. KOPR acts as a negative regulator of dopamine release in the PFC. Activation of the KOPR inhibits dopamine release, and if the KOPR activation exceeds physiological levels it could produce a hypo-dopaminergic state in the PFC (Carlezon et al., 2006 (Reference 13); Margolis et al., 2006 (Reference 40)). A hypodopaminergic state in the PFC is typically associated with ADHD (Cummings, 1993 (Reference 15); Biederman, 2005 (Reference 6)). Therefore, KOPR over-activation may be implicated in the ADHD hypodopaminergic state, and that blocking the KOPR may alleviate this condition. A prenatal nicotine exposure (PNE) mouse model has been developed, which shares behavioral (hyperactivity), neurochemical (PFC hypodopaminergic state), neuroanatomical (decreased cingulate cortex thickness), and pharmacological (responsiveness to MPH) features with human ADHD (Zhu et al 2012 (Reference 83)). In this model a PFC hypodopaminergic state is associated with hyperactivity and upregulation of KOPR activity. Moreover, the mixed opioid receptor antagonist naltrexone mitigates the hyperactivity. Based on these data, it appears that: (a) the hyperactivity and PFC hypodopaminergic state in the PNE mice is associated with selective upregulation of KOPR in the PFC; (b) selective KOPR antagonists mitigate the hyperactivity by alleviating the PFC hypodopaminergic state; and (c) unlike the classic stimulant compounds, the KOPR antagonists do not produce reinforcement or reward either to the KOPR antagonist itself or to stimulant compounds.

Figure 4:
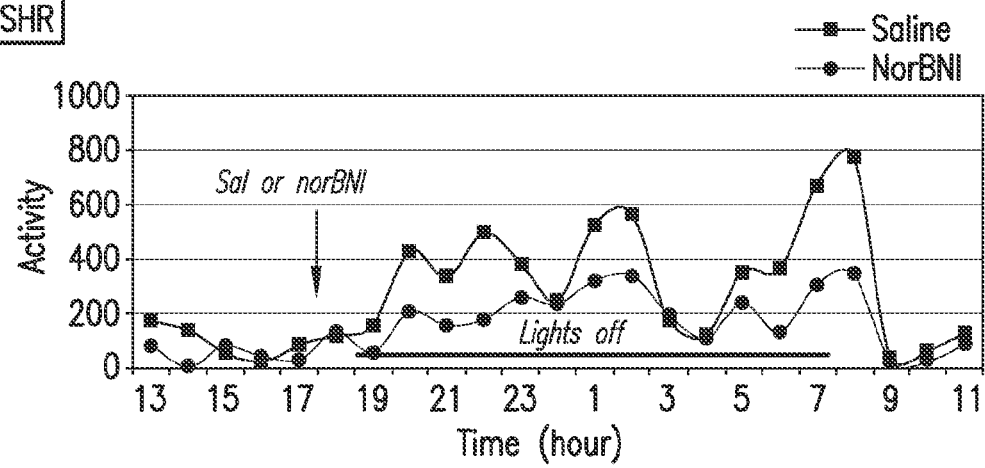
FIG. 4 shows a graph of the effects of nor-BNI on hyperactivity in the spontaneously hypertensive rat (SHR).
Figure 5:
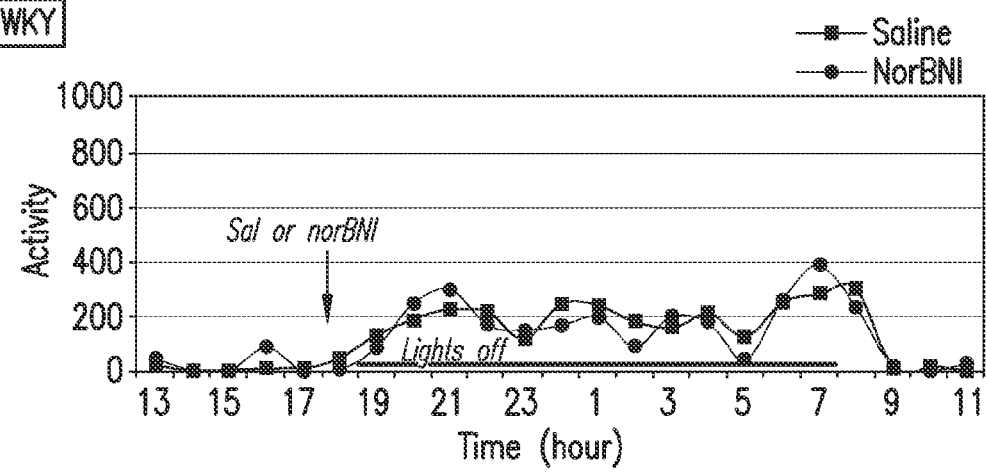
FIG. 5 shows a graph of the effects of nor-BNI on hyperactivity in a control (WKY) group of rats.

Spontaneously hypertensive rat (SHR) is another rodent model of ADHD (Sagvolden et al., 2009 (Reference 56)). This model also shows hyperactivity (Sagvolden et al., 2005 (Reference 56)) and increased KOPR activity in the frontal cortex (Bhargava and Gulati, 1988 (Reference 3)). FIGS. 4 and 5 show that administration of nor-BNI to this model decreases hyperactivity, a proxy behavior measure for ADHD. These findings confirm our prediction that KOPR antagonists are effective in mitigating ADHD-like symptoms in animal models.

Significance: Stimulants such as MPH [Ritalin®] and amphetamine [Adderal®] constitute mainstays of treatment for ADHD (Olfson, Marcus et al. 2002 (Reference 46); Brown, Amler et al. 2005 (Reference 10); Zuvekas, Vitiello et al. 2006 (Reference 84)). Although therapeutic effects of stimulants are well appreciated, with over one hundred studies documenting their safety and efficacy in pediatric and adult ADHD (Brown, Amler et al. 2005 (Reference 10)), serious concerns persist about their negative side effects, which can span the entire spectrum between euphoria leading to addiction and dysphoria leading to medication intolerance and eventually medication non-compliance (Biederman, Wilens et al. 1997 (Reference 4); Biederman, Wilens et al. 1998 (Reference 5); Klein-Schwartz 2002 (Reference 31); Robbins 2002 (Reference 53); Volkow 2006 (Reference 68)). The negative side effects appear to depend upon the dose and route of stimulant administration (Gerasimov and Volkova 1991 (Reference 24); Patrick and Markowitz 1997 (Reference 47); Kuczenski and Segal 2002 (Reference 34); Kuczenski and Segal 2005 (Reference 35)). The concerns about stimulant addiction are heightened by the finding that non-human primates self-administer stimulants (Bergman, Madras et al. 1989 (Reference 2)) just as they do cocaine, and recreational street-use of prescription stimulant medications is on the rise ((Bright 2008 (Reference 8)); New York Times, June 19th 20120. Therefore, there is serious concern that stimulant compounds, despite their therapeutic benefits, could also be harmful. The stigma of addiction and abuse, together with the Drug Enforcement Agency's classification of stimulant compounds as Schedule II drugs, limit public access and/or acceptance of these valuable therapeutic compounds, even for legitimate therapeutic use. As a result many ADHD patients remain untreated and add to public health and socio-economic burden to our society.

Kappa opioid receptor (KOPR) antagonists may increase PFC dopamine levels and as such work just as effectively as classic stimulant medications to alleviate the hypodopaminergic state associated with ADHD, and thereby ameliorating ADHD symptoms. However, in contrast to the stimulants, the KOPR antagonists will not carry the addiction or abuse risk because their CNS mechanism of action is different from that of the stimulants (FIG. 1). FIG. 1 shows a mechanism of action of the KOPR antagonist nor-BNI versus that of stimulants at PFC dopaminergic terminals. KOPR negatively regulates dopamine release. Nor-BNI and other KOPR antagonists block KOPR and facilitates dopamine release. On the other hand, stimulants such as MPH and cocaine block the dopamine transporter (DAT), reduce dopamine reuptake, and thus increase dopamine at the synapse. Amphetamines (Amp in FIG. 1) act via two mechanisms: (1) facilitate dopamine release and (2) block dopamine transporter and dopamine reuptake.

The KOPR antagonists relieve the normal inhibitory control over dopamine release at the synaptic terminal (Svingos, Chavkin et al. 2001 (Reference 59); Svingos, Garzon et al. 2001 (Reference 60)). Unlike stimulants (including cocaine), they do not block the dopamine transporter and do not produce reinforcing or rewarding effects (Todtenkopf, Marcus et al. 2004 (Reference 64)). Thus, the KOPR antagonists act via a distinct mechanism, and do not produce the rapid rise in dopamine levels ("high") associated with cocaine or high doses of prescription stimulants, which is the forerunner of addiction and abuse. Thus, the KOPR antagonists are non-stimulants and have the potential to be free from abuse liability. Non-stimulant treatments may rid ADHD medications of the stigma of addiction and obviate the federal regulatory restrictions associated with current ADHD treatments. Thus, it could make effective treatment readily available to millions of ADHD patients worldwide who currently do not receive it, and also minimize recreational or street-use of prescription stimulants.

Although the PFC hypo-dopaminergic state is a hallmark of ADHD, how it arises during development is not known. That KOPR overactivity contributes to the PFC hypo-dopaminergic state represents a novel etiologic mechanism of ADHD. In one embodiment of the present invention the KOPR mechanism may be exploited to provide a non-stimulant and abuse-free treatment for ADHD.

In one embodiment of the present invention, the KOPR mechanism may be exploited to provide a non-stimulant and abuse-free treatment for ADHD arising due to overactivity of the KOPR.

KOPR is one of three subtypes of opioid receptors, ($\mu$, $\delta$ and $\kappa$) (Evans, Keith et al. 1992 (Reference 22); Kieffer, Befort et al. 1992 (Reference 30); Li, Zhu et al. 1993 (Reference 36); Zhu, Chen et al. 1995 (Reference 80)), and it is predominantly localized to the presynaptic compartment, especially in dopaminergic terminals (Jomary, Gairin et al. 1992 (Reference 28); Drake, Patterson et al. 1996 (Reference 19); Meshul and McGinty 2000 (Reference 42); Svingos and Colago 2002 (Reference 61)). KOPR also co-localizes with the dopamine transporter (Thompson, Zapata et al. 2000 (Reference 63); Svingos, Chavkin et al. 2001 (Reference 59)). Preclinical studies show that KOPR activation negatively regulates dopamine release from meso-cortical terminals in the PFC (Chefer, Moron et al. 2000 (Reference 14); Margolis and Lock et al. 2006 (Reference 40)). Thus, it is plausible that over-activation of the PFC KOPR leads to a PFC hypodopaminergic state and that blocking the KOPR may elevate PFC dopamine levels and ameliorate the hypodopaminergic state.

Prenatal nicotine exposure (PNE) mouse model: Among the environmental risk factors associated with ADHD, maternal smoking during pregnancy ranks the highest (Milberger, Biederman et al. 1996 (Reference 44); Linnet, Dalsgaard et al. 2003 (Reference 37); Huizink and Mulder 2006 (Reference 27); Wickstrom 2007 (Reference 69); Pauly and Slotkin 2008 (Reference 49)). It has recently been shown that in a PNE mouse model spontaneous locomotor activity is significantly increased, dopamine turnover is significantly decreased (reflecting reduced extracellular dopamine) in the PFC and cingulate cortex volume is significantly reduced (Zhu, Zhang et al. 2012 (Reference 83)). Rodent models of PNE also show attention deficits (Schneider, Ilott et al. 2011 (Reference 57)). The increased locomotor activity occurs only during the active phase (lights off period) and a single oral administration of methylphenidate (MPH) reduces the activity to the levels seen in drug naïve control mice. The MPH administration also increases PFC dopamine turnover. These features of the mouse model recapitulate the key features of human ADHD at behavioral, neurochemical, anatomical, and pharmaco-therapeutic levels. A number of other animal models of ADHD have been described (Russell, Sagvolden et al. 2005 (Reference 54); Sagvolden, Russell et al. 2005 (Reference 56); Mill 2007 (Reference 45)). However none has fully withstood criticism about relevance to etiology, symptoms, underlying neuroanatomical changes or behavioral response to stimulants to the same extent as the PNE mouse model. Therefore the PNE mouse model was selected for the studies described in the examples below.

Figure 2:
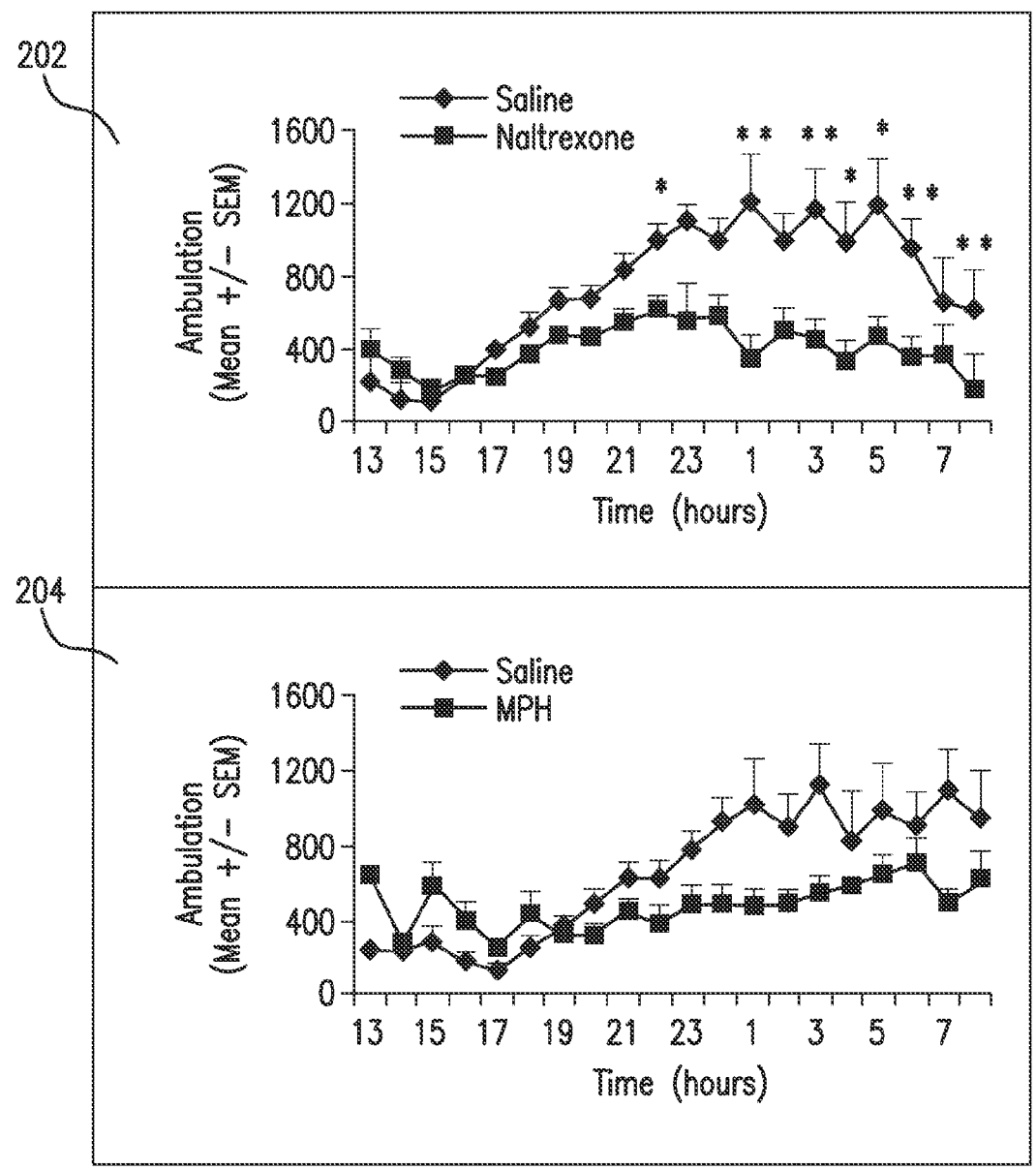
FIG. 2 shows a graph of the effects of naltrexone on hyperactivity in prenatally nicotine exposed (PNE) mice in comparison to a graph of the effects of methylphenidate (MPH) on hyperactivity in PNE mice.

Naltrexone decreases locomotor activity in the PNE mouse model: As part of a study examining the interactions between MPH and opioid receptors (Zhu et al 2011 (Reference 82)), naltrexone, a mixed opioid receptor antagonist, or MPH (classic stimulant) was administered to the PNE mice. Naltrexone (1 mg/kg, oral) was administered at 19:00 hrs to postnatal day 60 (P60) male PNE mice (n=13). The locomotor activity was recorded over an 18-hr period from 13:00 hrs to 08:00 hrs next day. Previous reports have indicated that oral naltrexone at this dose range (0.5-2 mg/kg) is effective in reducing hyperactivity in children (Campbell, Anderson et al. 1993 (Reference 12); Willemsen-Swinkels, Buitelaar et al. 1996 (Reference 71); Feldman, Kolmen et al. 1999 (Reference 23); Elchaar, Maisch et al. 2006 (Reference 20)). It has been found that naltrexone significantly reduces locomotor activity in the PNE mice compared to vehicle (graph 202 of FIG. 2). In a separate study (graph 204 of FIG. 2), therapeutic equivalent dose of MPH (0.75 mg/kg, oral; Balcioglu et al. 2010 (Reference 1)) also significantly decreased locomotor activity in the PNE mice. Thus, naltrexone produces an effect similar to that of MPH on locomotor activity. These results suggest that blocking the opioid receptors reduces locomotor activity in the PNE mice implicating opioid receptor activation in the etiology of the hyperactivity.

Figure 3:
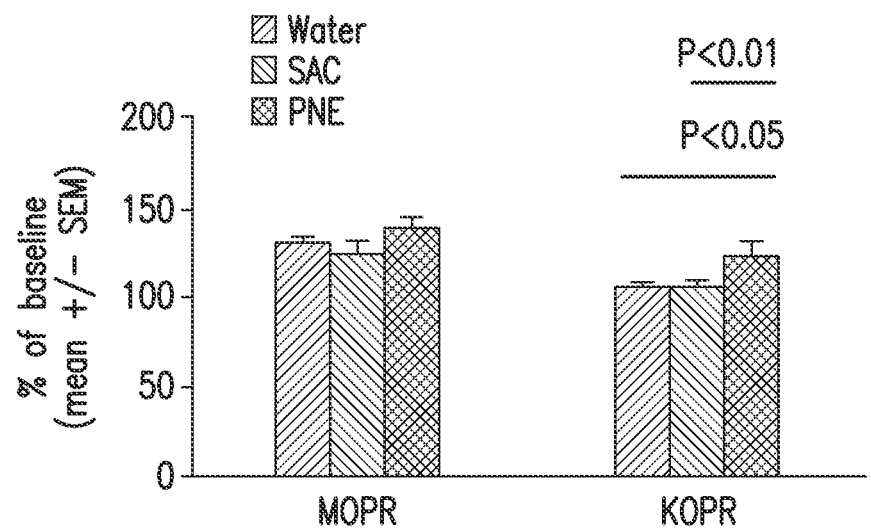
FIG. 3 shows a graph of MOPR and KOPR activities in the prefrontal cortex (PFC).

There is enhanced KOPR but not MOPR activity in the PFC of the PNE mice. Since naltrexone is a mixed opioid receptor antagonist, the identity of the opioid receptor ($\mu$, $\delta$ or $\kappa$) involved in naltrexone's effect on the hyperactivity phenotype remained unclear. One way to find this out is by verifying the opioid receptor that is elevated in the PFC of the PNE mice. Therefore, the expression of the two likely candidates, KOPR and MOPR in the PFC has been examined PFC membrane preparations obtained from P60 male mice from the PNE and two control groups, [saccharin (SAC) or plain water (Water); n=8 per group] were used. Receptor activity was measured using GTP$\gamma$S binding assay developed by us (Zhu et al 2011 (Reference 82)). U50,488H and DAMGO (10 $\mu$M each) were used as selective KOPR or MOPR agonist/stimulator, respectively. ANOVA revealed significant prenatal treatment effects on KOPR activity (one-ANOVA, F(2,23)=6.30, P<0.05) but not MOPR activity (ANOVA, F(2,23)=1.66, P>0.05 (FIG. 3). Tukey's Multiple Comparison Test revealed significant increase in KOPR activity in the PNE mice compared to controls (p<0.05), and no significant difference between the controls. These data indicate enhanced KOPR but not MOPR activity in the PFC of the PNE group.

Since administration of a mixed opioid receptor antagonist (such as naltrexone) without a CNS stimulant (such as methylphenidate) is effective in reducing hyperactivity in the PNE mouse model, and since only the KOPR is upregulated in the PNE mouse model, in one embodiment, the present invention provides a combination of KOPR antagonist and stimulant compounds such as MPH that act synergistically to produce greater therapeutic benefits in ADHD than either compound alone.

When administered as a combination for the treatment of ADHD, the dose of the CNS stimulant and the KOPR antagonist needed to produce therapeutic effects will be smaller and therefore safer than the dose that would be needed if the two compounds were administered alone.

In addition, the stimulant plus KOPR antagonist combination may be effective treatment for ADHD that does not respond to treatment with stimulants alone.

Spontaneously hypertensive rat (SHR) as an ADHD model. The SHR is a spontaneously occurring mutation associated with hypertension. However, the SHR rat also shows hyperactivity and attention deficits, and is widely used as a model for ADHD (Sagvolden et al., 2005 (Reference 46); Sagvolden et al., 2009 (Reference 56)). The SHR also shows increased KOPR activity in the frontal cortex (Bhargava and Gulati, 1988 (Reference 3)). Thus, both the SHR and the PNE mouse model show hyperactivity and increased frontal cortical KOPR activity. The selective KOPR antagonist, nor-BNI (10 mg/kg, i.p.) or the saline vehicle were administered to 60-day old SHR and WKY control rats (Sagvolden et al., 2009 (Reference 56)) at 17:00 hr and locomotor activity measured at hourly intervals over the next 19 hr (FIGS. 4 and 5). It was found that nor-BNI administration reduced the locomotor activity in the SHR compared to saline administration (FIG. 4). The same nor-BNI administration did not affect locomotor activity in the WKY control strain of rats (FIG. 5). Since the hyperactivity in the SHR rat was evident during the lights off period from 19:00 hr to 7:00 hr, activity was compared during the lights off period between SHR rats receiving nor-BNI and those receiving saline. It was found that nor-BNI produced significant reductions in locomotor activity in the SHR during the lights off period compared to saline (Mean±SEM beam breaks: Nor-BNI=2743.25±945.8; Saline=4830.75±609.2; t=2.61, df=6; p=0.04). Nor-BNI did not produce significant changes in activity levels in the WKY rats (Mean±SEM beam breaks: Nor-BNI=2494.75±831.6; Saline=2604.5±608.1; p>0.05). These data show that the selective KOPR antagonist nor-BNI reduces hyperactivity in the SHR rats and does not produce significant effects on the activity in the WKY control rats.

The decrease in hyperactivity produced by a single i.p. injection of nor-BNI (10 mg/kg) in the SHR rat was observed for a period of 21 days. The long-lasting effects of nor-BNI in the SHR is consistent with previous reports that the desensitization of the KOPR produced by nor-BNI lasts for up to 21 days (Metcalf and Coop, 2005 (Reference 43); Patkar et al., 2013 (Reference 48)).

The results of the studies described above suggest that KOPR activity is upregulated in the PFC of the PNE mice and the SHR and that blockade of KOPR activity ameliorates the hyperactivity. These findings lend support to the hypothesis that elevated KOPR activity in the PFC contributes to the PFC hypodopaminergic state/hyperactivity and that selective KOPR blockade ameliorates the hypodopaminergic state and hyperactivity.

It is important to establish that the hypothesized increases in PFC dopamine level following selective KOPR antagonism do not produce rewarding effects. A rat model showed that KOPR antagonist did not produce rewarding effects despite increased CNS dopamine levels (Todtenkopf, Marcus et al. 2004 (Reference 64)). A likely explanation for the lack of rewarding effects is that the increase in dopamine level was modest [(~175%) (Maisonneuve, Archer et al. 1994 (Reference 39)). In contrast, cocaine, MPH or amphetamine can induce 500-1000% increase in dopamine (Di Chiara and Imperato 1988 (Reference 17); Maisonneuve, Archer et al. 1994 (Reference 39)).

Finally, naltrexone is FDA approved for the treatment of alcohol and opiate dependence. Since naltrexone can reduce the hyperactivity in the PNE mice just as well as MPH, why not use naltrexone as the novel ADHD treatment? That is, what is the rationale for proposing to test nor-BNI or other selective KOPR antagonists over naltrexone? Recent preclinical evidence suggests that the endogenous opioid system is critical for normal brain development, especially for cell proliferation (Zagon and McLaughlin 1983 (Reference 75); Zagon and McLaughlin 1983 (Reference 76); Hauser, McLaughlin et al. 1987 (Reference 25); Zagon 1987 (Reference 74); Zagon and McLaughlin 1987 (Reference 77)). Naltrexone can adversely impact these developmental events because of its ability to block multiple opioid receptors (McLaughlin, Sassani et al. 2010 (Reference 41); Donahue, McLaughlin et al. 2011 (Reference 18)). Naltrexone also leads to reduced weight gain upon long-term usage (Recant, Voyles et al. 1980 (Reference 51)). These drawbacks limit its use in children, a segment of the population most frequently affected by ADHD. Further, since naltrexone blocks the MOPR it has the further complication of preventing therapeutic use of MOPR agonist compounds (such as opioid compounds) for pain relief. Therefore, development of an alternative is critical. It is proposed that the alternative is a selective KOPR antagonist because the hyperactivity and the PFC hypodopaminergic state are likely the result of elevated KOPR and not MOPR or DOPR activities.

In one embodiment, a single administration of the present invention the kappa opioid receptor (KOPR) antagonists as efficacious treatment for ADHD for up to one month. The long lasting efficacy is due to long term desensitization of the KOPR by the single administration of the KOPR antagonist.

Various methods may be used to administer nor-BNI to an individual. For example, in one embodiment of the present invention nor-BNI may be administered intranasally. In other embodiments of the present invention, nor-BNI may be administered orally, via a transdermal patch or via a sublingual bolus.

In one embodiment of the present invention, the reduction in symptoms of ADHD may be confirmed by neuro-psychological evaluation.

To avoid potential side effects of the treatment of the present invention, the amount of nor-BNI administered to an individual on a daily or monthly basis may be minimized. In one embodiment of the present invention, the amount of nor-BNI administered to an individual per dose may 1 to 20 mg/kg. In one embodiment of the present invention, the amount of nor-BNI administered to an individual per dose may be 1 to 10 mg/kg. In one embodiment of the present invention, the amount of nor-BNI administered to an individual per dose may be 1 to 5 mg/kg. In one embodiment of the present invention, the amount of nor-BNI administered to an individual per dose may be 1 mg of nor-BNI per kg.

In one embodiment, an individual may be treated with nor-BNI with a daily dose of nor-BNI for a period of one day or at regular intervals until the symptoms of the disorder can be controlled without the aid of nor-BNI.

Suitable nontoxic pharmaceutically acceptable carriers for use in a drug delivery system for intranasal administration of nor-BNI may include: an aqueous solution or physiological saline. The choice of suitable carriers will depend on the exact nature of the particular nasal dosage form desired, e.g., whether no-BNI is to be formulated into a nasal solution (for use as drops or as a spray).

Having described the many embodiments of the present invention in detail, it will be apparent that modifications and variations are possible without departing from the scope of the invention defined in the appended claims. Furthermore, it should be appreciated that all examples in the present disclosure, while illustrating many embodiments of the invention, are provided as non-limiting examples and are, therefore, not to be taken as limiting the various aspects so illustrated.

EXAMPLES

Example 1

The following hypotheseses are tested: (a) systemic administration of the selective KOPR antagonist nor-binaltorphimine (nor-BNI) reduces hyperactivity in the PNE mice to the level seen in saline-administered controls; (b) repeated nor-BNI administration maintains the reduced activity level, and that (c) repeated nor-BNI administration does not promote conditioned place preference (a surrogate measure of addiction) to cocaine, MPH or nor-BNI its elf.

Experimental Design

Female C57Bl/6 mice are administered (−)-Nicotine (0.1 mg/ml) plus 2% saccharin in drinking water starting 3 weeks prior to mating and throughout pregnancy. Control groups include mice receiving either 2% saccharin in drinking water (SAC) or plain drinking water without additives (Water). Nor-BNI is injected intraperitoneally to P60 mice one day prior to analysis of locomotor activity (Knoll, Meloni et al. 2007 (Reference 32)) because its blockade of KOPR lasts for 7 to 10 days (Endoh, Matsuura et al. 1992 (Reference 21); Jones and Holtzman 1992 (Reference 29)). A dose of 10 or 20 mg/kg nor-BNI is used, a dose range known to produce selective KOPR blockade (Takemori, Ho et al. 1988 (Reference 62); Wiley, Poveromo et al. 2009 (Reference 70)). PNE, SAC and Water groups are in every Experiments 1A, 1B and 1C below, unless stated otherwise.

Experiment 1A

The specific aim of this experiment is to test whether nor-BNI can reduce hyperactivity in PNE mice and to determine the duration of the effect following a single administration. On day 1, saline is administered at 19:00 hrs and on day 2 locomotor activity is recorded from 19:00 hrs to 7:00 hrs (lights-off period) to obtain a measure of basal activity. On day 3, nor-BNI (1, 5, 10 or 20 mg/kg, intraperitoneal (i.p.)) or saline is administered at 19:00 hr. On each of days 4 to 34 locomotor activity is recorded from 19:00 hrs to 7:00 hrs. Thus basal activity is recorded on day 2 and, on each of days 4-34 (30 days) nor-BNI induced activity is analyzed. The effect of nor-BNI as percentage of the basal activity (percent inhibition) is calculated. The activities for different nor-BNI doses (0-20 mg/kg) on each of days 4-34 are analyzed. These studies test whether nor-BNI has an effect on locomotor activity and the duration of the effects of a single administration.

Experiment 1B

The specific aim of this experiment is to test if repeated nor-BNI administration to the PNE group can maintain the reduced activity level if Experiment 1A showed that one injection of nor-BNI was effective in reducing activity level for only a few days (fewer than 30 days, for example). A saline injection on day 1 yields basal activity. The saline injection is followed by injections of nor-BNI or saline. The dose of nor-BNI and interval between the injections is based on data from Experiment 1A on the duration of efficacy of a single nor-BNI injection. Percent inhibition for each nor-BNI injection is calculated as described in Experiment 1A.

Experiment 1C

The specific aim of this experiment is to test if repeated nor-BNI administration described in Experiment 1B promotes conditioned place preference (CPP) for cocaine, MPH or nor-BNI Example 2

The overall aim of the experiments of this example is to test the hypothesis that increased KOPR but not MOPR or DOPR activity in the PFC underlies the hyperactivity in the PNE mice. The experiments of this example involve testing if the reduction in locomotor activity in the PNE mice produced by the non-selective opioid receptor antagonist naltrexone (FIG. 2) can be reversed by administration of the selective KOPR agonist (U50,488H) systemically or directly into the PFC but not by similar administrations of the MOPR agonist, Fentanyl, or the DOPR agonist BW373U86. The direct administration of the drugs to the PFC tests drug action in the PFC as the potential cause of any change in the locomotor activity. As shown by graph 202 and graph 204 of FIG. 2, naltrexone, a mixed opioid receptor antagonist, reduces hyperactivity in PNE mice in a manner comparable to that of methylphenidate (MPH) (n=8-12, t-test, **p<0.01, *p<0.05).

Experimental Design

The PNE mouse model is used for the experiments of this example. Locomotor activity is analyzed following administration of the different drugs based on the design in Aim 1. PNE, SAC and Water groups are used in every experiment, unless stated otherwise.

Experiment 2A

The specific aim of this experiment is to test if the effects of naltrexone on hyperactivity in the PNE mice (FIG. 2) can be reversed by systemic administration of U50,488H (KOPR agonist), Fentanyl (MOPR agonist) or BW373U86 (DOPR agonist). Naltrexone (1 mg/kg, oral) administration is followed immediately by U50,488H (10 mg/kg, i.p.) (Bolanos, Garmsen et al. 1996 (Reference 7)), Fentanyl (1 mg/kg, i.p.) (Zhu, Xue et al. 1996 (Reference 81); Dean, Todtenkopf et al. 2008 (Reference 16); Bryant, Roberts et al. 2009 (Reference 11)), or BW373U86 (5 mg/kg, i.p.) (Broom, Jutkiewicz et al. 2002 (Reference 9)). A parallel set of mice receive saline alone or saline and each of the opioid receptor agonists. The drug administration is at 19:00 hr. Locomotor activity is monitored from 19:00 to 07:00 hr.

Experiment 2B

The specific aim of this experiment is to test if the effect of naltrexone on hyperactivity in the PNE mice can be reversed by microinjections of U50,488H (10 μM) (You, Herrera-Marschitz et al. 1999 (Reference 73)), DAMGO (0.1 μg/lμl) (Hellman, Mendelson et al. 2009 (Reference 26); Mahler and Berridge 2012 (Reference 38)) or DPDPE (1.5 μg/1 μl) (Randall-Thompson, Pescatore et al. 2010 (Reference 50)) directly into the PFC. The mice are implanted with cannulae in the PFC one week before the drug administration. Naltrexone is administered orally as in Experiment 2A, and each of the three opioid receptor agonists are microinjected (separately in parallel sets of mice) into the PFC. Locomotor activity is monitored as in Experiment 2A.

Experiment 2C

The specific aim of this experiment is to test if the hyperactivity in PNE mice is influenced by direct injection of KOPR antagonist, nor-BNI, MOPR antagonist, CTAP or DOPR antagonist, naltrindole into the PFC. The mice are implanted with cannulae one week before drug administration. Nor-BNI 5 μg/1 μl) (Zhu, Xue et al. 1996 (Reference 81); You, Herrera-Marschitz et al. 1999 (Reference 73); Varaschin and Morato 2009 (Reference 65)), CTAP (4 μg/1 μl) (Soderman and Unterwald 2008 (Reference 58) naltrindole (4 μg/1 μl) (Varaschin and Morato 2009 (Reference 65)), or saline is microinjected into the PFC at 19:00 hr. Locomotor activity assay is the same as in Experiment 2A. Collectively experiments 2A, 2B and 2C can be used to verify selective and PFC-specific (Experiments 2B and 2C) effects of KOPR on locomotor activity.

Example 3

The overall aim of the experiments of this example is to test the hypothesis that spontaneous dopamine release in the PFC of PNE mice is significantly lower than that in the SAC control group (representing a PFC hypodopaminergic state in the PNE mice), and that administration of nor-BNI or MPH systemically or directly into the PFC increases the PFC dopamine release in both groups of mice compared to saline administration via the same routes. The direct administration of the drugs to the PFC tests drug action in the PFC as the potential cause of any change in dopamine release.

Experimental Design

The PNE mouse model is used. Microdialysis is performed as described in the following publications, the entire contents and disclosure of which are incorporated herein by reference: Zhu, J. M., X. P. He, et al. 1990 (Reference 79); Zhang et al. 2007 (Reference 78); Ren, J. Q., Y. Jiang, et al. 2011 (Reference 52). Dopamine, norepinephrine and serotonin levels are assayed with HPLC-EC. Twenty four hours after surgery for probe placement, mice are injected with saline (i.p.) and dialysate is collected for assessment of baseline monoamine concentration. On day 2 mice are injected with nor-BNI (10 or 20 mg/kg, based on the results of Example 1), MPH (0.75 mg/kg), naltrexone (1 mg/kg), U50,488H (dose: based on results of Example 2) or saline. Dialysates are collected for analysis.

Methods

Materials (−)-Nicotine, Saccharin, and all the opioid receptor agonists and antagonists is purchased from Sigma (St. Louis, Mo.).

Prenatal Nicotine Exposure

Female C57Bl/6 mice is administered (−)-Nicotine (0.1 mg/ml) plus 2% saccharin in drinking water starting 3 weeks prior to mating and throughout pregnancy. The male breeders are not be exposed to nicotine. Control groups include mice receiving either 2% saccharin in drinking water or plain drinking water without additives. On the day of birth (postnatal day 0; P0), offspring is cross-fostered to drug-naïve nursing mothers. In each experiment 12 mice from each group are used. Not more than one offspring from any litter is used, to minimize the contribution of litter effects on the data [details in (Zhu and Zhang et al. 2012 (Reference 83))].

Locomotor Activity

On the day of analysis, the mice is removed from their home cages and individually placed in the testing cages equipped with photobeam motion sensors (Photobeam Activity System; San Diego Instruments, San Diego, Calif.). Each instance in which consecutive breaks is recorded in adjacent photobeams (positioned 5.4 cm apart) is scored as an ambulatory event. Photobeam breaks is grouped into hourly activity measurements for statistical analysis. See also Zhu, J., Zhang, X., et al. "Prenatal nicotine exposure mouse model showing hyperactivity, reduced cingulate cortex volume, reduced dopamine turnover, and responsiveness to oral methylphenidate treatment." *J. Neurosci.* 32(27): 9410-18 (2012) (Reference 83).

Conditioned Place Preference (CPP)

A three-chamber place preference apparatus (Med Associates Inc., St. Albans Vt., USA) is used. The CPP procedure includes three phases: preconditioning, conditioning and test phases. The pre-conditioning phase is performed on day 1 (two sessions daily, AM and PM), mice is initially placed in the central gray chamber for 2 min and then allowed free access to the white and black chambers for 20 min. The time spent in each chamber is recorded. During the conditioning phase, the non-preferred chamber (i.e. the chamber in which less time is spent during pre-conditioning phase) is designated as the test drug-paired chamber, while the preferred chamber is designated as the vehicle-paired chamber. The conditioning phase is carried out for 3 days from day 2-4. There is two conditioning sessions daily, morning or afternoon session, with at least 4 hour interval between them. There is one session each for saline-paired and drug-paired conditions for each day during this phase. The mice is administered saline or the drug [cocaine 5, 10 and 20 mg/kg, MPH 2, 5 and 7.5 mg/kg or nor-BNI 25, 35 and 50 mg/kg) in the saline- or drug-paired sessions, respectively and placed in the central gray chamber for 2 min and then confined to the saline- or drug-paired chamber, respectively for 30 min. Each mouse is treated for two sessions including a saline-session and a drug-session each day. The order of treatments for saline or drug is reversed on a daily basis. The test day is on day 5 (one session, AM). The difference between time spent in the drug-paired chamber during the test phase and pre-conditioning phases is calculated as the CPP score. Effective doses of cocaine and MPH have been previously established (Zhu, Spencer et al. 2011 (Reference 82)). It is proposed that an up to 5-fold higher dose of nor-BNI than that estimated to be effective in reducing the hyperactivity.

In Vivo Microdialysis and High Performance Liquid Chromatography with Electrochemical Detection (HPLC-ECD)

Mice are anesthetized with ketamine/xylazine (100/10 mg/kg) and a microdialysis probe is implanted into the right prefrontal cortex (+2.1 mm anteroposterior, +1.0 mm mediolateral from the bregma, and −1.2 mm dorsoventral with respect to dura). Probe is secured onto the skull using stainless-steel screws and dental acrylic. Probes are perfused continuously with artificial CSF (147 mM NaCl, 4 mM KCl, and 2.3 mM CaCl2) at a rate of 1.5 µl/min. Dialysates are collected every 20 min for 1 h. Twenty four hours after surgery, mice are injected with saline (i.p.) and dialysate are collected immediately after injection for one hour as baseline measurement. On the 2nd day mice are injected with the various drugs. Dialysates are collected starting immediately after injection and then every 20 min for one hour. There are the following groups: (1) saline+saline, (2) saline+nor-BNI, (3) saline+MPH, (4) saline+naltrexone, (5) saline+U50,488 for each PNE, SAC and water groups. A total of 15 groups are created [3 pretreatment (PNE, SAC and Water)×5 treatment=15 groups]. At the end of each experiment, mice are perfused with 4% paraformaldehyde and brains removed and sectioned into 50 nm thick sections using Vibratome. Sections are stained with Nissl for analysis of probe placement. Data from animals with correct probe placement only are used. The final (usable) number of mice is 12 per group.

Concentrations of dopamine, norepinephrine and serotonin are analyzed using an isocratic method with electrochemical detection and a Varian Microsorb-MV reverse-phase column (150×4.6 mm, C18, Sum pore size). The mobile phase is based on the MD-TM mobile phase (ESA Biosciences, Dionex Corp) and composed of 75 mM sodium phosphate, 1.75 mM 1-octanesulfonate sodium salt, 100 µl/L triethylamine, 25 µM EDTA, and 10% acetonitrile. The flow rate is 0.6 ml/min and the injection volume of each sample is 20 µl. Detection is performed using a coulometric cell with an analytical potential of +225 mV. Data collection is performed by a CouloChem II detector and EZChrom Elite Software. Concentration of analysates is determined using a standard curve at the beginning of every run. DHBA is used as an internal standard to correct for minor variations between biological samples in each run.

PFC Microinjection

Mice are implanted with cannula in the PFC using stereotactic coordinates as described above for microdialysis. Drug administration into the PFC are as described above for each experiment.

Data Analysis

Differences between multiple treatment groups are analyzed for statistical significance using one, two or three-way ANOVA. When significant difference (p<0.05) is found by ANOVA, a multiple comparison post hoc Test (Tukey) are performed to identify groups differing significantly from each other.

Expected Results from Experiments in Examples 1, 2 and 3

It is expected that the increased locomotor activity in the PNE mice will be reduced to control levels following nor-BNI administration (i.p.) at 10 or 20 mg/kg (Experiment 1A).

It is expected that repeated nor-BNI will maintain the control level activity throughout the 4-week experimental period (Experiment 1B).

It is expected that repeated nor-BNI administration will not enhance CPP for cocaine, MPH or nor-BNI (Experiment 1C). These expectations, if confirmed will offer pre-clinical data in support of nor-BNI as a novel drug that can reduce hyperactivity in the PNE model and that does not produce drug addiction.

It is expected that the effects of nor-BNI on locomotor activity will be brain region specific, in that direct injections into the PFC are expected to produce the same or similar effects on locomotor activity as the i.p. injection.

It is expected that that the microdialysis experiments will show that PNE produces a PFC hypodopaminergic state, which will be ameliorated by selective blockade of the KOPR using i.p. and PFC-specific injections of nor-BNI.

REFERENCES

The following references are referred to above and/or describe technology that may be used with the present invention and are incorporated herein by reference:

1. Balcioglu, A., Ren, J-Q., McCarthy, D. M., Spencer, T. J., Biederman, J., Bhide, P. G. Plasma and brain concentrations of oral therapeutic doses of methylphenidate and their impact on brain monoamine content in mice. *Neuropharmacology* 102:783-88 (2009).
2. Bergman, J., Madras, B. K., et al. "Effects of cocaine and related drugs in nonhuman primates. III. Self-administration by squirrel monkeys." *J. Pharmacol. Exp. Ther.* 251(1): 150-55 (1989).
3. Bhargava, H. N., Gulati A, "Kappa opioid receptor activity in spontaneously hypertensive rats," *The Journal of Pharmacology and Experimental Therapeutics* 245: 460-465 (1988).
4. Biederman, J., T. Wilens, et al. "Is ADHD a risk factor for psychoactive substance use disorders? Findings from a four-year prospective follow-up study." *J. Am. Acad. Child. Adolesc. Psychiatry* 36(1): 21-29 (1997).
5. Biederman, J., Wilens, T. E., et al. "Does attention-deficit hyperactivity disorder impact the developmental course of drug and alcohol abuse and dependence?" *Biol. Psychiatry* 44(4): 269-73 (1998).
6. Biederman, J. "Attention-deficit/hyperactivity disorder: a selective overview." *Biol. Psychiatry* 57(11): 1215-20 (2005).
7. Bolanos, C. A., Garmsen, G. M., et al., "Effects of the kappa-opioid receptor agonist U-50,488 on morphine-induced place preference conditioning in the developing rat." *Eur. J. Pharmacol.* 317(1): 1-8 (1996).
8. Bright, G. M. "Abuse of medications employed for the treatment of ADHD: results from a large-scale community survey." *Medscape J. Med.* 10(5): 111 (2008).
9. Broom, D. C., Jutkiewicz, E. M., et al. (2002). "Nonpeptidic delta-opioid receptor agonists reduce immobility in the forced swim assay in rats." *Neuropsychopharmacology* 26(6): 744-55.
10. Brown, R. T., Amler, R. W., et al. "Treatment of attention-deficit/hyperactivity disorder: overview of the evidence." *Pediatrics* 115(6): e749-57 (2005).
11. Bryant, C. D., Roberts, K. W., et al. "Pavlovian conditioning of multiple opioid-like responses in mice." *Drug Alcohol Depend.* 103(1-2): 74-83 (2009).
12. Campbell, M., Anderson, L. T., et al. "Naltrexone in autistic children: behavioral symptoms and attentional learning." *J. Am. Acad. Child Adolesc. Psychiatry* 32(6): 1283-91 (1993).
13. Carlezon, W. A., Jr., Beguin, C., et al. "Depressive-like effects of the kappa-opioid receptor agonist salvinorin A on behavior and neurochemistry in rats." *J. Pharmacol. Exp. Ther.* 316(1): 440-47 (2006).
14. Chefer, V. I., Moron, J. A., et al. "Kappa-opioid receptor activation prevents alterations in mesocortical dopamine neurotransmission that occur during abstinence from cocaine." *Neuroscience* 101(3): 619-27 (2000).
15. Cummings, J. L. "Frontal-subcortical circuits and human behavior." *Arch. Neurol.* 50(8): 873-80 (1993).
16. Dean, R. L., Todtenkopf, M. S. et al. "Overriding the blockade of antinociceptive actions of opioids in rats treated with extended-release naltrexone." *Pharmacol. Biochem. Behav.* 89(4): 515-22 (2008).
17. Di Chiara, G. and Imperato, A. "Drugs abused by humans preferentially increase synaptic dopamine concentrations in the mesolimbic system of freely moving rats." *Proc. Natl. Acad. Sci. USA* 85(14): 5274-78 (1988).
18. Donahue, R. N., McLaughlin, P. J., et al. "Low-dose naltrexone targets the opioid growth factor-opioid growth factor receptor pathway to inhibit cell proliferation: mechanistic evidence from a tissue culture model." *Exp. Biol. Med. (Maywood)* 236(9): 1036-50 (2011).
19. Drake, C. T., Patterson, T. A., et al. "Kappa opioid receptor-like immunoreactivity in guinea pig brain: ultrastructural localization in presynaptic terminals in hippocampal formation." *J. Comp. Neurol.* 370(3): 377-95 (1996).
20. Elchaar, G. M., Maisch, N. M., et al. "Efficacy and safety of naltrexone use in pediatric patients with autistic disorder." *Ann. Pharmacother.* 40(6): 1086-95 (2006).
21. Endoh, T., Matsuura, H., et al. "Nor-binaltorphimine: a potent and selective kappa-opioid receptor antagonist with long-lasting activity in vivo." *Arch. Int. Pharmacodyn. Ther.* 316: 30-42 (1992).
22. Evans, C. J., Keith, D. E., Jr., et al. "Cloning of a delta opioid receptor by functional expression." *Science* 258 (5090): 1952-55 (1992).
23. Feldman, H. M., Kolmen, B. K., et al. "Naltrexone and communication skills in young children with autism." *J. Am. Acad. Child Adolesc. Psychiatry* 38(5): 587-93 (1999).
24. Gerasimov, A. A. and Volkova, A. M. "[Treatment of patients with lumbar osteochondrosis by the method of intra-tissular electric stimulation]." *Ortop. Travmatol. Protez.* (5): 13-17 (1991).
25. Hauser, K. F., McLaughlin, P. J., et al. "Endogenous opioids regulate dendritic growth and spine formation in developing rat brain." *Brain Res.* 416(1): 157-61 (1987).
26. Hellman, K. M., Mendelson, S. J., et al. "Opioid microinjection into raphe magnus modulates cardiorespiratory function in mice and rats." *Am. J. Physiol. Regul. Integr. Comp. Physiol.* 297(5): R1400-08 (2009).
27. Huizink, A. C. and Mulder, E. J. "Maternal smoking, drinking or cannabis use during pregnancy and neurobehavioral and cognitive functioning in human offspring." *Neurosci. Biobehav. Rev.* 30(1): 24-41 (2006).
28. Jomary, C., Gairin, J. E., et al. "Synaptic localization of kappa opioid receptors in guinea pig neostriatum." *Proc. Natl. Acad. Sci. USA* 89(2): 564-68 (1992).
29. Jones, D. N. and Holtzman, S. G. "Long term kappa-opioid receptor blockade following nor-binaltorphimine." *Eur. J. Pharmacol.* 215(2-3): 345-48 (1992).
30. Kieffer, Befort, B. L., K., et al. "The delta-opioid receptor: isolation of a cDNA by expression cloning and pharmacological characterization." *Proc. Natl. Acad. Sci. USA* 89(24): 12048-52 (1992).
31. Klein-Schwartz, W. "Abuse and toxicity of methylphenidate." *Curr. Opin. Pediatr.* 14(2): 219-23 (2002).
32. Knoll, A. T., Meloni, E. G., et al. "Anxiolytic-like effects of kappa-opioid receptor antagonists in models of 33. Kuczenski, R. and Segal, D. S. "Locomotor effects of acute and repeated threshold doses of amphetamine and methylphenidate: relative roles of dopamine and norepinephrine." *J. Pharmacol. Exp. Ther.* 296(3): 876-83 (2001).

34. Kuczenski, R. and Segal, D. S. "Exposure of adolescent rats to oral methylphenidate: preferential effects on extracellular norepinephrine and absence of sensitization and cross-sensitization to methamphetamine."*J. Neurosci.* 22(16): 7264-71 (2002).

35. Kuczenski, R. and Segal, D. S. "Stimulant actions in rodents: implications for attention-deficit/hyperactivity disorder treatment and potential substance abuse." *Biol. Psychiatry* 57(11): 1391-96 (2005).

36. Li, S., Zhu, J., et al. "Molecular cloning and expression of a rat kappa opioid receptor." *Biochem. J.* 295 (Pt 3): 629-33 (1993).

37. Linnet, K. M., Dalsgaard, S., et al. "Maternal lifestyle factors in pregnancy risk of attention deficit hyperactivity disorder and associated behaviors: review of the current evidence." *Am. J. Psychiatry* 160(6): 1028-40 (2003).

38. Mahler, S. V. and K. C. Berridge (2012). "What and when to "want"? Amygdala-based focusing of incentive salience upon sugar and sex." *Psychopharmacology (Berl)* 221(3): 407-426.

39. Maisonneuve, I. M., Archer, S., et al. "U50,488, a kappa opioid receptor agonist, attenuates cocaine-induced increases in extracellular dopamine in the nucleus accumbens of rats." *Neurosci. Lett.* 181(1-2): 57-60 (1994).

40. Margolis, E. B., Lock, H., et al. "Kappa opioids selectively control dopaminergic neurons projecting to the prefrontal cortex." *Proc. Natl. Acad. Sci. USA* 103(8): 2938-42 (2006).

41. McLaughlin, P. J., Sassani, J. W., et al. "Diabetic keratopathy and treatment by modulation of the opioid growth factor (OGF)-OGF receptor (OGFr) axis with naltrexone: a review." *Brain Res. Bull.* 81(2-3): 236-47 (2010).

42. Meshul, C. K. and McGinty, J. F. "Kappa opioid receptor immunoreactivity in the nucleus accumbens and caudate-putamen is primarily associated with synaptic vesicles in axons." *Neuroscience* 96(1): 91-99 (2000).

43. Metcalf M D, Coop A, "Kappa opioid antagonists: past successes and future prospects," *The AAPS journal* 7:E704-722 (2005).

44. Milberger, S., Biederman, J., et al. "Is maternal smoking during pregnancy a risk factor for attention deficit hyperactivity disorder in children?" *Am. J. Psychiatry* 153(9): 1138-42 (1996).

45. Mill, J. "Rodent models: Utility for candidate gene studies in human attention-deficit hyperactivity disorder (ADHD)." *J. Neurosci. Methods* 166(2):294-305 (2007).

46. Olfson, M., Marcus, S. C., et al. "National trends in the use of psychotropic medications by children." *J. Am. Acad. Child. Adoles.c Psychiatry* 41(5): 514-21 (2002).

47. Patrick, K. S. and Markowitz, J. S. "Pharmacology of methylphenidate, amphetamine enantiomers and pemoline in attention-deficit hyperactivity disorder." *Human Psychopharmacol.* 12(6): 527-46 (1997).

48. Patkar, K. A., Wu, J., Ganno, M. L., Singh, H. D., Ross, N. C., Rasakham, K., Toll, L., McLaughlin, J. P., "Physical Presence of Nor-Binaltorphimine in Mouse Brain over 21 Days after a Single Administration Corresponds to Its Long-Lasting Antagonistic Effect on kappa-Opioid Receptors," *The Journal of pharmacology and experimental therapeutics* 346:545-554 (2013).

49. Pauly, J. R. and Slotkin, T. A. "Maternal tobacco smoking, nicotine replacement and neurobehavioural development." *Acta Paediatr.* 97(10): 1331-37 (2008).

50. Randall-Thompson, J. F., Pescatore, K. A., et al. "A role for delta opioid receptors in the central nucleus of the amygdala in anxiety-like behaviors." *Psychopharmacology (Berl)* 212(4): 585-95 (2010).

51. Recant, L., Voyles, N. R., et al. "Naltrexone reduces weight gain, alters "beta-endorphin", and reduces insulin output from pancreatic islets of genetically obese mice." *Peptides* 1(4): 309-13 (1980).

52. Ren, J. Q., Jiang, Y., et al. "Prenatal L-DOPA exposure produces lasting changes in brain dopamine content, cocaine-induced dopamine release and cocaine conditioned place preference." *Neuropharmacology* 60(2-3): 295-302 (2011).

53. Robbins, T. W. "ADHD and addiction." *Nat. Med.* 8(1): 24-25 (2002).

54. Russell, V. A., Sagvolden, T., et al. "Animal models of attention-deficit hyperactivity disorder." *Behav. Brain Funct.* 1: 9 (2005).

55. Sagvolden, T., Russell, V. A., et al. "Rodent models of attention-deficit/hyperactivity disorder." *Biol. Psychiatry* 57(11): 1239-47 (2005).

56. Sagvolden T, Johansen E B, Woien G, Walaas S I, Storm-Mathisen J, Bergersen L H, Hvalby O, Jensen V, Aase H, Russell V A, Killeen P R, Dasbanerjee T, Middleton F A, Faraone S V, "The spontaneously hypertensive rat model of ADHD—the importance of selecting the appropriate reference strain," *Neuropharmacology* 57:619-626 (2009).

57. Schneider, T., Ilott, N., et al. "Prenatal exposure to nicotine impairs performance of the 5-choice serial reaction time task in adult rats." *Neuropsychopharmacology* 36(5): 1114-25 (2011).

58. Soderman, A. R. and Unterwald, E. M. "Cocaine reward and hyperactivity in the rat: sites of mu opioid receptor modulation." *Neuroscience* 154(4): 1506-16 (2008).

59. Svingos, A. L., Chavkin, C., et al. "Major coexpression of kappa-opioid receptors and the dopamine transporter in nucleus accumbens axonal profiles." *Synapse* 42(3): 185-92 (2001).

60. Svingos, A. L., Garzon, M., et al. "Mu-opioid receptors in the ventral tegmental area are targeted to presynaptically and directly modulate mesocortical projection neurons." *Synapse* 41(3): 221-29 (2001).

61. Svingos, A. L. and Colago, E. E. "Kappa-Opioid and NMDA glutamate receptors are differentially targeted within rat medial prefrontal cortex." *Brain Res.* 946(2): 262-71 (2002).

62. Takemori, A. E., Ho, B. Y., et al. "Nor-binaltorphimine, a highly selective kappa-opioid antagonist in analgesic and receptor binding assays." *J. Pharmacol. Exp. Ther.* 246(1): 255-58 (1988).

63. Thompson, A. C., Zapata, A., et al. "Kappa-opioid receptor activation modifies dopamine uptake in the nucleus accumbens and opposes the effects of cocaine." *J. Neurosci.* 20(24): 9333-40 (2000).

64. Todtenkopf, M. S., Marcus, J. F., et al. "Effects of kappa-opioid receptor ligands on intracranial self-stimulation in rats." *Psychopharmacology (Berl)* 172(4): 463-70 (2004).

65. Varaschin, R. K. and Morato, G. S. "Selective mu- and kappa-opioid receptor antagonists administered into the nucleus accumbens interfere with rapid tolerance to ethanol in rats." *Psychopharmacology (Berl)* 206(1): 85-96 (2009).
66. Volkow N. D., Fowler J. S., Gatley S J, Dewey S L, Wang G J, Logan J, Ding Y S, Franceschi D, Gifford A, Morgan A, Pappas N, King P, "Comparable changes in synaptic dopamine induced by methylphenidate and by cocaine in the baboon brain." *Synapse* 31:59-66 (1999).
67. Volkow, N. D., Wang, G. J., et al. "Methylphenidate and cocaine have a similar in vivo potency to block dopamine transporters in the human brain." *Life Sci.* 65(1): PL7-12 (1999).
68. Volkow, N. D. "Stimulant medications: how to minimize their reinforcing effects?" *Am. J. Psychiatry* 163(3): 359-61 (2006).
69. Wickstrom, R. "Effects of nicotine during pregnancy: human and experimental evidence." *Current neuropharmacology* 5(3): 213-22 (2007).
70. Wiley, M. D., Poveromo, L. B., et al. "Kappa-opioid system regulates the long-lasting behavioral adaptations induced by early-life exposure to methylphenidate." *Neuropsychopharmacology* 34(5): 1339-50 (2009).
71. Willemsen-Swinkels, S. H., Buitelaar, J. K., et al. "The effects of chronic naltrexone treatment in young autistic children: a double-blind placebo-controlled crossover study." *Biol. Psychiatry* 39(12): 1023-31 (1996).
72. Yano, M. and Steiner, H. "Methylphenidate and cocaine: the same effects on gene regulation?" *Trends Pharmacol. Sci.* 28(11): 588-596 (2007).
73. You, Z. B., Herrera-Marschitz, M., et al. "Modulation of neurotransmitter release in the basal ganglia of the rat brain by dynorphin peptides." *J. Pharmacol. Exp. Ther.* 290(3): 1307-15 (1999).
74. Zagon, I. S. "Endogenous opioids, opioid receptors, and neuronal development." *NIDA Res. Monogr.* 78: 61-71 (1987).
75. Zagon, I. S. and McLaughlin, P. J. "Increased brain size and cellular content in infant rats treated with an opiate antagonist." *Science* 221(4616): 1179-80 (1983).
76. Zagon, I. S. and McLaughlin, P. J. "Naltrexone modulates growth in infant rats." *Life Sci.* 33(24): 2449-54 (1983).
77. Zagon, I. S. and McLaughlin, P. J. "Endogenous opioid systems regulate cell proliferation in the developing rat brain." *Brain Res.* 412(1): 68-72 (1987).
78. Zhang, L., Shirayama, Y., et al. "Minocycline attenuates hyperlocomotion and prepulse inhibition deficits in mice after administration of the NMDA receptor antagonist dizocilpine." *Neuropsychopharmacology* 32(9): 2004-10 (2007).
79. Zhu, J. M., X. P. He, et al. "Changes of releases of beta-endorphin-like immunoreactive substances and noradrenaline in rabbit's preoptic area during acupuncture analgesia." *Sheng Li Xue Bao* 42(2): 188-93 (1990).
80. Zhu, J., Chen, C. et al. "Cloning of a human kappa opioid receptor from the brain." *Life Sci.* 56(9): PL201-07 (1995).
81. Zhu, J., Xue, J. C., et al. "The region in the mu opioid receptor conferring selectivity for sufentanil over the delta receptor is different from that over the kappa receptor." *FEBS Lett.* 384(2): 198-202 (1996).
82. Zhu, J., Spencer, T. J., et al. "Methylphenidate and mu opioid receptor interactions: a pharmacological target for prevention of stimulant abuse." *Neuropharmacology* 61(1-2): 283-92 (2011).
83. Zhu, J., Zhang, X., et al. "Prenatal nicotine exposure mouse model showing hyperactivity, reduced cingulate cortex volume, reduced dopamine turnover, and responsiveness to oral methylphenidate treatment." *J. Neurosci.* 32(27): 9410-18 (2012).
84. Zuvekas, S. H., Vitiello, B., et al. "Recent trends in stimulant medication use among U.S. children." *Am. J. Psychiatry* 163(4): 579-85 (2006).

While the present invention has been disclosed with references to certain embodiments, numerous modification, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A method comprising:
   administering an effective amount of nor-binaltorphimine (nor-BNI) or a nor-BNI analog in the absence of a stimulant to an individual having Attention Deficit/Hyperactivity Disorder (ADHD), thereby reducing the symptoms of the disorder in the individual.

2. The method of claim 1, wherein the individual does not respond to treatment with a stimulant.

3. The method of claim 1, wherein the individual has ADHD caused at least in part by over-activity of a kappa opioid receptor.

4. The method of claim 1, wherein the nor-BNI or nor-BNI analog is administered intranasally to the individual.

5. The method of claim 1, wherein the nor-BNI or nor-BNI analog is administered orally to the individual.

6. The method of claim 1, wherein the nor-BNI or nor-BNI analog is administered by injection into the individual.

7. The method of claim 1, wherein the nor-BNI or nor-BNI analog is administered via transdermal patch to the individual.

8. The method of claim 1, wherein the nor-BNI or nor-BNI analog is administered via sublingual bolus to the individual.

9. The method of claim 1, wherein the effective amount of nor-BNI or a nor-BNI analog is 1 to 20 mg/kg.

10. The method of claim 1, wherein the effective amount of nor-BNI or a nor-BNI analog is 1 to 10 mg/kg.

11. The method of claim 1, wherein the effective amount of nor-BNI or a nor-BNI analog is 1 to 5 mg/kg.

12. The method of claim 1, wherein the nor-BNI or nor-BNI analog is administered to the individual on a daily basis until the symptoms of ADHD are controlled without the aid of the nor-BNI or nor-BNI analog.

13. The method of claim 1, wherein the nor-BNI or nor-BNI analog is administered to the individual on a weekly basis until the symptoms of ADHD are controlled without the aid of the nor-BNI or nor-BNI analog.

14. The method of claim 1, wherein the nor-BNI or nor-BNI analog is administered to the individual on a monthly basis until the symptoms of ADHD are controlled without the aid of the nor-BNI or nor-BNI analog.

15. The method of claim 1, wherein the individual has ADHD as defined by DSM IV, IV-TR, or V.

16. The method of claim 1, wherein nor-BNI is administered to the individual.

17. The method of claim 1, wherein the nor-BNI analog is selected from the group consisting of (3R)-7-Hydroxy-N-[(1 S)-1-[[(3R,4R)-4-(3-hydroxyphenyl)-3,4-dimethyl-1-piperidinyl]methyl]-2-methylpropyl]-1,2,3,4-tetrahydro-3- isoquinoline-carboxamide, Alvimopan, LY255.582, AZ-MTAB, PF4455242, and LY2456302.

18. The method of claim 1, wherein a reduction in the symptoms of the attention disorder is measured using an ADHD rating scale.

* * * * *